United States Patent [19]

Butler

[11] Patent Number: 5,618,834
[45] Date of Patent: Apr. 8, 1997

[54] INDOLE DERIVATIVES IN THE TREATMENT OF EMESIS

[75] Inventor: Paul Butler, Ramsgate, England

[73] Assignee: Pfizer Inc., New York, N.Y.

[21] Appl. No.: 565,425

[22] Filed: Nov. 30, 1995

[30] Foreign Application Priority Data

Dec. 3, 1994 [GB] United Kingdom ............... 9424471

[51] Int. Cl.$^6$ ................... A61K 31/395; A61K 31/445; A61K 31/405
[52] U.S. Cl. .................. 514/415; 514/210; 514/323; 514/872
[58] Field of Search ................... 514/210, 323, 514/415, 872

[56] References Cited

FOREIGN PATENT DOCUMENTS 9206973  4/1992  WIPO .

OTHER PUBLICATIONS

Hannington-Kiff, *Anaesthesia*, 48, 144–146 (1993).

*Primary Examiner*—Kimberly Jordan
*Attorney, Agent, or Firm*—Peter C. Richardson; Paul H. Ginsburg; Grover F. Fuller, Jr.

[57] ABSTRACT

Compounds of formula I,

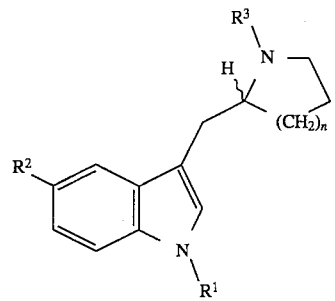

wherein $R^1$ represents hydrogen; $R^2$ represents hydrogen, halogen, cyano, $OR^4$, $-(CH_2)_m CONR^5 R^6$, $-(CH_2)_m SO_2 NR^5 R^6$, $-(CH_2)_m NR^7 COR^8$, $-(CH_2)_m S(O)_x R^8$, $-(CH_2)_m NR^7 CONR^5 R^6$, $-(CH_2)_m NR^7 COOR^9$ or $-CH=CH(CH_2)_y R^{10}$; $R^3$ represents hydrogen or $C_{1-6}$ alkyl; $R^4$ represents hydrogen, $C_{1-6}$ alkyl or aryl; $R^5$ and $R^6$ are independently represent hydrogen, $C_{1-6}$ alkyl, aryl or $(C_{1-3}$ alkyl)aryl; or $R^5$ and $R^6$ taken together may form a 4-, 5- or 6-membered ring; $R^7$ and $R^8$ independently represent hydrogen, $C_{1-6}$ alkyl, aryl or $(C_{1-3}$ alkyl)aryl; $R^9$ represents hydrogen, $C_{1-6}$ alkyl, aryl or $(C_{1-3}$ alkyl)aryl; $R^{10}$ represents $-CONR^5 R^6$, $-SO_2 NR^5 R^6$, $-NR^7 COR^8$, $-NR^7 SO_2 R^8$, $-NR^7 CONR^5 R^6$, $-S(O)_x R^8$ or $-NR^7 COOR^9$; m is 0, 1, 2 or 3; n is 0, 1 or 2; y is 0, 1 or 2; x is 1 or 2; and pharmaceutically acceptable salts thereof; are useful in the treatment or prevention of emesis not associated with migraine.

7 Claims, No Drawings

INDOLE DERIVATIVES IN THE TREATMENT OF EMESIS

This invention relates to the use of certain indole derivatives in the treatment or prevention of emesis.

International Patent Application WO 92/06973 discloses a series of indole derivatives which are potent serotonin (5-HT$_1$) agonists. These compounds are useful for treating disorders arising from deficient serotonergic neurotransmission including hypertension, depression, anxiety, eating disorders, obesity, drug abuse, cluster headache, migraine, pain, chronic paroxysmal hemicrania and headache associated with vascular disorders. They are of particular interest as therapeutic agents for treatment of migraine.

Sumatriptan [3-(2-N,N-dimethylaminoethyl)-5-methylaminosulphonylmethyl-1H-indole], a compound of related structure, is also a 5-HT$_1$ receptor agonist and is known to be effective in the treatment of migraine. It is known that sumatriptan relieves headache, nausea, photophobia and phonophobia in a majority of acute migraine patients. Sumatriptan does not readily cross the blood/brain barrier and this is evidence that sumatriptan activates peripheral inhibitory receptors resembling the 5-HT$_{1D}$ subtype located on perivascular nerves within the meninges and which, when activated, prevent neuropeptide release and impulse conduction in trigeminovascular fibers (Moskowitz and Cutrer, Ann Rev Med, 1993, 44, 145–54). Sumatriptan is thus believed to have a "peripheral" site of action in treating vascular headache and associated symptoms. Recently, sumatriptan has been shown to relieve and prevent post-operative nausea and vomiting (Anaesthesia, 1993, Vol 48, pp 144–146).

It has now been found that the indole compounds of WO 92/06973 are effective in treating or preventing emesis even in the absence of a migraine attack. This is unexpected as the emetic response per se is believed to be centrally, not peripherally, controlled.

Thus, according to the present invention, there is provided the use of a compound of formula I,

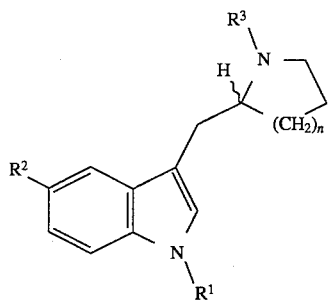

wherein $R^1$ represents hydrogen;

$R^2$ represents hydrogen, halogen (e.g. fluorine, chlorine, bromine or iodine), cyano, $OR^4$, $-(CH_2)_mCONR^5R^6$, $-(CH_2)_mSO_2NR^5R^6$, $-(CH_2)_mNR^7COR^8$, $-(CH_2)_mS(O)_xR^8$, $-(CH_2)_mNR^7CONR^5R^6$, $-(CH_2)_mNR^7COOR^9$ or $-CH=CH(CH_2)_yR^{10}$;

$R^3$ represents hydrogen or $C_{1-6}$ alkyl;

$R^4$ represents hydrogen, $C_{1-6}$ alkyl or aryl;

$R^5$ and $R^6$ are independently represent hydrogen, $C_{1-6}$ alkyl, aryl or ($C_{1-3}$ alkyl)aryl;

or $R^5$ and $R^6$ taken together may form a 4-, 5- or 6-membered ring;

$R^7$ and $R^8$ independently represent hydrogen, $C_{1-6}$ alkyl, aryl or ($C_{1-3}$ alkyl)aryl;

$R^9$ represents hydrogen, $C_{1-6}$ alkyl, aryl or ($C_{1-3}$ alkyl)aryl;

$R^{10}$ represents $-CONR^5R^6$, $-SO_2NR^5R^6$, $-NR^7COR^8$, $-NR^7SO_2R^8$, $-NR^7CONR^5R^6$, $-S(O)_xR^8$ or $-NR^7COOR^9$;

m is 0, 1, 2 or 3;

n is 0, 1 or 2;

y is 0, 1 or 2;

x is 1 or 2;

or a pharmaceutically acceptable salt thereof;

in the manufacture of a medicament for the treatment or prevention of emesis;

characterized in that the emesis is not associated with migraine.

Pharmaceutically acceptable salts include non-toxic acid addition salts, i.e. salts containing pharmacologically acceptable anions. Some salts are mentioned in WO 92/06973, which also describes methods of preparing the compounds mentioned above and formulations containing the compounds for administration to patients. Fumarate salts are of particular interest.

Alkyl groups which $R^{3-9}$ may represent or comprise may be linear or branched.

Aryl groups which $R^{4-9}$ may represent or comprise are independently selected from phenyl and substituted phenyl. Substituted phenyl groups may be substituted with one to three groups selected from $C_{1-4}$ alkyl, halogen (e.g., fluorine, chlorine, bromine or iodine), hydroxy, cyano, carboxamido, nitro and $C_{1-4}$ alkoxy.

A further aspect of the invention provides a method of treating or preventing emesis not associated with migraine which comprises administering to a patient an effective amount of a compound of formula I, as defined above, or a pharmaceutically acceptable salt thereof; and said compound or salt for use in treating emesis not associated with migraine.

Preferred groups of compounds which may be mentioned are those in which:

(a) $R^2$ is $-(CH_2)_mSO_2NHR^5$, $-(CH_2)_mNHSO_2R^8$, $-(CH_2)_mSO_2R^8$, $-(CH_2)_mCONHR^5$ or $-(CH_2)_mNHCOR^8$; and (b) $R^3$ is H or methyl.

Particularly preferred compounds are:

(R)-5-(methylaminosulphonylmethyl)-3-(N-methylpyrrolidin-2-ylmethyl)-1H-indole, (R)-5-(methylaminosulphonylmethyl)-3-(pyrrolidin-2-ylmethyl)-1H-indole, (R)-5-(aminosulphonylmethyl)-3-(N-methylpyrrolidin-2-ylmethyl)-1H-indole and (R)-5-(2-phenylsulphonylethyl)-3-(N-methylpyrrolidin-2-ylmethyl)-1H-indole; and their pharmaceutically acceptable salts.

The compounds of formula I may exist as optical isomers, and the use of all such isomers, and mixtures thereof, are included within the scope of the invention. However, compounds having (R)-stereochemistry, as shown in formula IA,

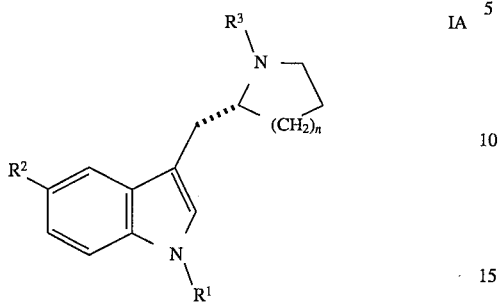

in which $R^{1-3}$ and n are as defined above, are preferred.

The compounds of formula I, and their pharmaceutically acceptable salts may be formulated in a conventional manner using one or more pharmaceutically acceptable carriers. Thus the active compounds may be formulated for oral, buccal, intranasal, parenteral (e.g. intravenous, intramuscular or subcutaneous) or rectal administration, or in a form suitable for inhalation or insufflation. Formulation methods are described in International Patent Application WO 92/06973.

The daily dose of the compound of formula I, or its pharmaceutically acceptable salt, administered to a patient for treatment or prevention of emesis will be determined by a physician for any given patient but in general it will be similar to the dosage recommended for treatment of migraine (typically 0.1–200 mg of active ingredient per unit oral, parenteral or buccal dose which could be administered, for example, 1 to 4 times daily for an adult weighing 70 kg). In an aerosol formulation each metered dose or "puff" may contain from 20 μg to 1000 μg of the compound and the overall daily dose will be from 100 μg to 10 mg. However, it has been found that (R)-5-(methylaminesulphonylmethyl)-3-(N-methylpyrrolidin-2-ylmethyl-1H-indole, (R)-5-(methylaminosulphonylmethyl)-3-(pyrrolidin-2-ylmethyl)-1H-indole and (R)-5-(aminosulphonylmethyl)-3-(pyrrolidin-2-ylmethyl)-1H-indole are active at doses several orders of magnitude less. The typical unit dose for oral, parenteral or buccal administration will then be 0.1 μg to 200 mg for these compounds with a correspondingly reduced dose for aerosol formulations.

It is believed that the compounds of formula I, and their pharmaceutically acceptable salts are efficacious against emesis caused by several factors not associated with migraine, including emesis induced by anaesthesia (post-operative nausea and vomiting), cancer chemotherapy and by motion (seasickness, space and airsickness). Emesis induced by anaesthesia (post-operative nausea and vomiting) is of particular interest.

The activity of the compounds as anti-emetics may be demonstrated by the method of Tatersall et al. and Bountra et al. (European Journal of Pharmacology, 250 (1993) R5 and 249 (1993) R3–R4). In this method the extent to which they reduce the latency or the number of retches and/or vomits induced by emetogens in the conscious ferret compared with vehicle-treated animals is measured. For example, it has been found that (R)-5-(methylaminosulphonylmethyl)-3-(N-methylpyrrolidin-2-ylmethyl)-1H-indole (300 μg/kg, i.v.) but not sumatriptan (300 μg/kg, i.v.) causes a delay in the latency to the first retch or vomit induced by cis-platin.

I claim:

1. A method of treatment or prevention of emesis, which comprises administering a therapeutically effective amount of a compound of formula I,

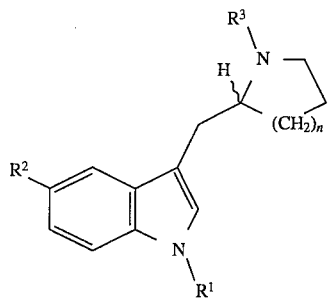

wherein $R^1$ represents hydrogen;

$R^2$ represents hydrogen, halogen, cyano, $OR^4$, $-(CH_2)_mCONR^5R^6$, $-(CH_{2m}SO_2NR^5R^6$, $-(CH_2)_mNR^7COR^8$, $-(CH_2)_mS(O)_xR^8$, $-(CH_2)_mNR^7CONR^5R^6$, $-(CH_2)_mNR^7COOR^9$ or $-CH=CH(CH_2)_yR^{10}$;

$R^3$ represents hydrogen or $C_{1-6}$ alkyl;

$R^4$ represents hydrogen, $C_{1-6}$ alkyl or aryl;

$R^5$ and $R^6$ are independently represent hydrogen, $C_{1-6}$ alkyl, aryl or $(C_{1-3}$ alkyl)aryl;

or $R^5$ and $R^6$ taken together may form a 4-, 5- or 6-membered ring;

$R^7$ and $R^8$ independently represent hydrogen, $C_{1-6}$ alkyl, aryl or $(C_{1-3}$ alkyl)aryl;

$R^9$ represents hydrogen, $C_{1-6}$ alkyl, aryl or $(C_{1-3}$ alkyl)aryl;

$R^{10}$ represents $-CONR^5R^6$, $-SO_2NR^5R^6$, $-NR^7COR^8$, $-NR^7SO_2R^8$, $-NR^7CONR^5R^6$, $-S(O)_xR^8$ or $-NR^7COOR^9$;

m is 0, 1, 2 or 3;

n is 0, 1 or 2;

y is 0, 1 or 2;

x is 1 or 2;

or a pharmaceutically acceptable salt thereof;

to a patient in need thereof;

characterized in that the emesis is not associated with migraine.

2. The method as claimed in claim 1, wherein $R^2$ represents $-(CH_2)_mSO_2NHR^5$, $-(CH_2)_mNHSO_2R^8$, $-(CH_2)_mSO_2R^8$, $-(CH_2)_mCONHR^5$ or $-(CH_2)_mNHCOR^8$.

3. The method as claimed in claim 1 or claim 2, wherein $R^3$ is H or methyl.

4. The method as claimed in claim 1, wherein the compound of formula I has (R)-stereochemistry.

5. The method as claimed in claim 1, wherein the compound of formula 1 is:

(R)-5-(methylaminosulphonylmethyl)-3-(N-methylpyrrolidin-2-ylmethyl)-1H-indole, (R)-5-(methylaminosuiphonylmethyl)-3-(pyrrolidin-2-ylmethyl)-1H-indole, (R)-5-(aminosulphonylmethyl)-3-(N-methylpyrrolidin-2-ylmethyl)-1H-indole, or (R)-5-(2-phenylsulphonylethyl)-3-(N-methylpyrrolidin-2-ylmethyl)-1H-indole;

or a pharmaceutically acceptable salt thereof.

6. The method as claimed in claim 1, wherein the compound of formula I is in the form of its fumarate salt.

7. The method as claimed in claim 1, wherein the emesis is post-operative nausea and vomiting.

* * * * *